(12) United States Patent
Biedermann et al.

(10) Patent No.: US 7,963,994 B2
(45) Date of Patent: Jun. 21, 2011

(54) INTERVERTEBRAL DISK PROSTHESIS

(75) Inventors: Lutz Biedermann, Villingen (DE); Jurgen Harms, Karlsruhe (DE)

(73) Assignee: Biedermann Motech GmbH, VS-Schwenningen (DE)

( * ) Notice: Subject to any disclaimer, the term of this patent is extended or adjusted under 35 U.S.C. 154(b) by 406 days.

(21) Appl. No.: 10/660,452

(22) Filed: Sep. 11, 2003

(65) Prior Publication Data

US 2004/0117021 A1  Jun. 17, 2004

(30) Foreign Application Priority Data

Sep. 12, 2002 (DE) .................... 102 42 329

(51) Int. Cl.
*A61F 2/44* (2006.01)
(52) U.S. Cl. ................ 623/17.13; 623/17.14; 623/17.15
(58) Field of Classification Search .... 623/17.13–17.15, 623/17
See application file for complete search history.

(56) References Cited

U.S. PATENT DOCUMENTS

| | | | |
|---|---|---|---|
| 4,759,766 A | 7/1988 | Buetnner-Janz et al. | |
| 4,820,305 A | 4/1989 | Harms et al. | 623/16 |
| 4,932,975 A * | 6/1990 | Main et al. | 623/17.12 |
| 5,314,477 A | 5/1994 | Marnay | 623/17 |
| 5,370,697 A | 12/1994 | Baumgartner | 623/17 |
| 5,401,269 A | 3/1995 | Buttner-Janz et al. | 623/17 |
| 5,507,816 A | 4/1996 | Bullivant | 623/17 |
| 5,540,688 A * | 7/1996 | Navas | 606/61 |
| 5,609,637 A | 3/1997 | Biedermann et al. | |
| 5,676,701 A | 10/1997 | Yuan et al. | 623/17 |
| 5,702,451 A | 12/1997 | Biedermann et al. | 623/17 |
| 5,989,290 A | 11/1999 | Biedermann et al. | |
| 6,375,682 B1 * | 4/2002 | Fleischmann et al. | 623/17.12 |
| 6,527,804 B1 | 3/2003 | Gauchet et al. | 623/17.12 |
| 6,682,562 B2 | 1/2004 | Viart et al. | 623/17.14 |
| 6,764,512 B2 | 7/2004 | Keller | 623/11.11 |
| 6,936,071 B1 | 8/2005 | Marnay et al. | 623/17.15 |
| 7,066,958 B2 * | 6/2006 | Ferree | 623/17.12 |
| 7,235,102 B2 * | 6/2007 | Ferree et al. | 623/17.12 |
| 2001/0016773 A1 | 8/2001 | Serhan et al. | 623/17.15 |
| 2002/0128715 A1 * | 9/2002 | Bryan et al. | 623/17.15 |
| 2003/0045939 A1 | 3/2003 | Casutt | 623/17.15 |
| 2004/0024460 A1 | 2/2004 | Ferree | 623/17.12 |
| 2004/0153157 A1 | 8/2004 | Keller | 623/17.14 |

(Continued)

FOREIGN PATENT DOCUMENTS

DE  2 263 842  7/1974

(Continued)

OTHER PUBLICATIONS

U.S. Appl. No. 60/379,462, filed May 10, 2002.*

(Continued)

*Primary Examiner* — David H. Willse
(74) *Attorney, Agent, or Firm* — Christie, Parker & Hale, LLP

(57) ABSTRACT

An intervertebral disk prosthesis is disclosed. The intervertebral disk prosthesis is has a base plate, a top plate opposite the base plate, and an intervening core located between the top plate and base plate. One of the plates has a first concave contact face facing the core, which has a adjacent first convex contact face. A groove is provided around one of contact faces in which an elastic ring is placed. When placed in the groove, the elastic ring is also in contact with the opposite contact face.

16 Claims, 3 Drawing Sheets

U.S. PATENT DOCUMENTS

| | | | |
|---|---|---|---|
| 2005/0085917 A1 | 4/2005 | Marnay et al. | 623/17.16 |
| 2005/0251260 A1 | 11/2005 | Gerber et al. | 623/171.13 |
| 2005/0267581 A1 | 12/2005 | Marnay et al. | 623/17.14 |

FOREIGN PATENT DOCUMENTS

| | | |
|---|---|---|
| DE | 28 04 936 A1 | 2/1978 |
| DE | 30 23 353 A1 | 6/1980 |
| DE | 30 23 353 C2 | 6/1980 |
| DE | 35 29 761 C2 | 8/1985 |
| DE | 42 08 116 A1 | 3/1992 |
| DE | 42 13 771 C1 | 4/1992 |
| DE | 41 09 941 A1 | 10/1992 |
| DE | 299 11 422 U1 | 7/1999 |
| EP | 0 356 112 A1 | 8/1989 |
| EP | 0 610 837 B1 | 2/1994 |
| EP | 1 346 709 A2 | 9/2003 |
| JP | 49-11836 | 3/1974 |
| JP | 2001-526083 | 12/2001 |
| WO | WO 95/26697 A1 | 10/1995 |
| WO | WO 99/32055 | 7/1999 |
| WO | WO 01/68003 A1 | 9/2001 |
| WO | WO 02/11650 A2 | 2/2002 |

OTHER PUBLICATIONS

Derwent English Abstract of DE29911422U1, Jul. 1999.
Derwent English Abstract of DE 42 13 771, Apr. 1992.
Derwent English Abstract of DE 42 08 116, Mar. 1992.
Derwent English Abstract of DE 35 29 761 C2, previously filed in Information Disclosure Statement filed Apr. 19, 2006.
Derwent English Abstract of DE 30 23 353 C2, previously filed in Information Disclosure Statement filed Apr. 19, 2006.
Derwent English Abstract of DE 28 04 936 A1, previously filed in Information Disclosure Statement filed Apr. 19, 2006.

* cited by examiner

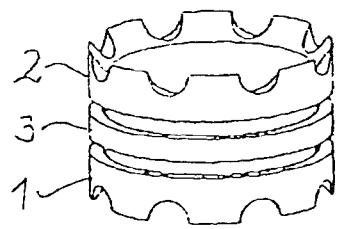
Fig. 1
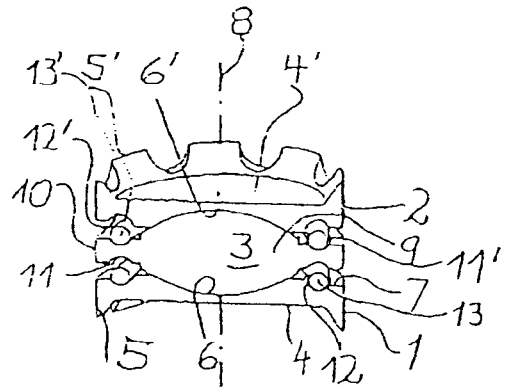
Fig. 2
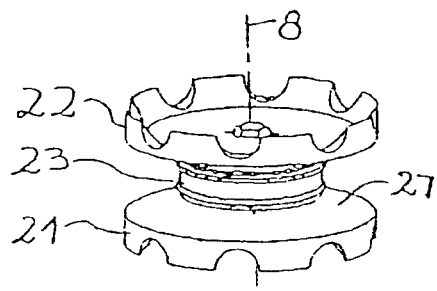
Fig. 3
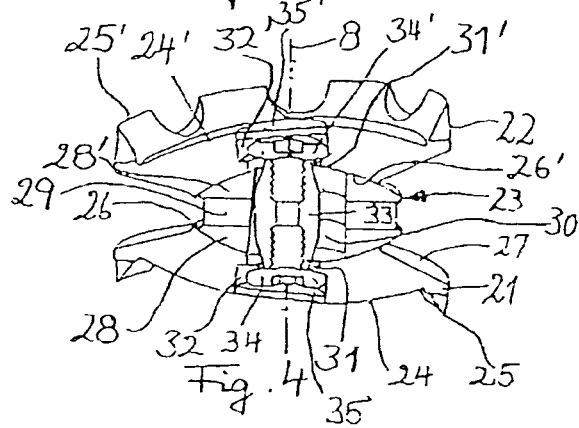
Fig. 4
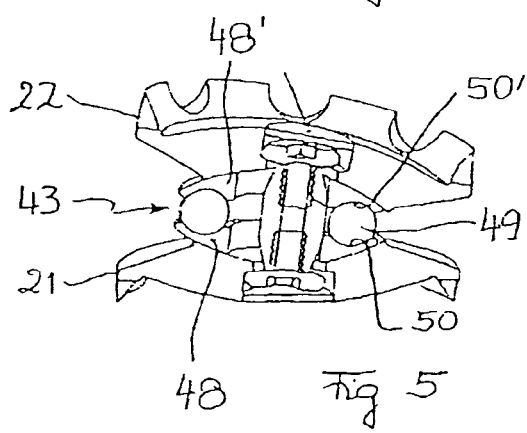
Fig. 5
Fig. 6
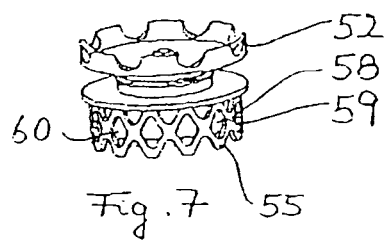
Fig. 7

INTERVERTEBRAL DISK PROSTHESIS

BACKGROUND

The invention relates to an intervertebral disk prosthesis with a bone plate, a top plate opposite said base plate and an intervening core.

An intervertebral disk prosthesis is described in DE 42 08 116 C. Similarly, EP 0 471 821 B describes an intervertebral disk prosthesis with a core which is spherical on one side. In spite of these intervertebral disk prosthesis, there still is a need for a intervertebral disk prosthesis which simulates a vertebral disk.

BRIEF SUMMARY

An object of the present invention is to create an intervertebral disk prosthesis which has a base plate, a top plate opposite the base plate and an intervening core between the top plate and base plate.

In one embodiment, the intervertebral disk prosthesis, according to the instant invention, provides for damping in the end region of the prosthesis, when the prosthesis is subject to tilting movement. In another embodiment, vertical damping is improved while axial rotation limited.

Advantages of the present invention will become readily apparent to those skilled in the art from the following description of the preferred embodiments of the invention which have been shown and described by way of illustration. As will be realized, the invention is capable of other and different embodiments, and its details are capable of modification in various respects. Accordingly, the drawings and description are to be regarded as illustrative in nature and not as restrictive.

BRIEF DESCRIPTION OF THE DRAWINGS

FIG. 1 shows a perspective side view of a first embodiment of the intervertebral disk prosthesis.

FIG. 2 shows a cross-sectional view of the embodiment shown in FIG. 1 of the intervertebral disk prosthesis.

FIG. 3 shows a perspective side view of a second embodiment of the intervertebral disk prosthesis.

FIG. 4 shows a cross-sectional view of the embodiment of the intervertebral disk prosthesis shown in FIG. 3.

FIG. 5 shows a cross-sectional view of a third embodiment of the intervertebral disk prosthesis.

FIG. 6 shows a cross-sectional of a fourth embodiment of the intervertebral disk prosthesis.

FIG. 7 shows a perspective view of the embodiment of the intervertebral disk prosthesis shown in FIG. 6.

DETAILED DESCRIPTION OF THE DRAWINGS AND THE PRESENTLY PREFERRED EMBODIMENTS

Figure 8:
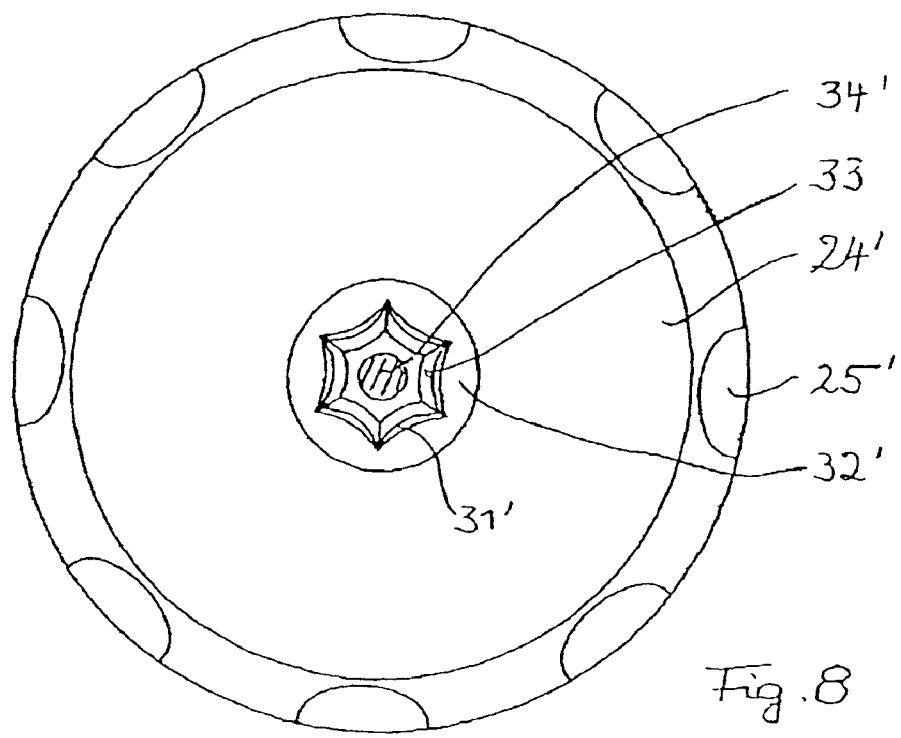
FIGS. 8 to 10 show enlarged horizontal plan views of a detail of the intervertebral disk prosthesis of the instant invention

Various aspects of the invention are presented in FIGS. 1-11, which are not drawn to scale, and wherein like components are numbered alike. Referring now to FIGS. 1-1, representations of the basic concepts according to certain aspects of the invention are now presented. Literal interpretation of the configurations presented in FIGS. 1-11 is not intended to limit the invention to the specific arrangements presented, as other variations or modifications are possible that are evident to persons skilled in the art of the description provided herein.

As can be seen from the figures, each embodiment of the intervertebral disk prosthesis has a base plate 1, a top plate 2 opposite the base plate, and an intervening core 3 positioned between the base plate 1 and top plate 2.

In a first embodiment, shown in FIGS. 1 and 2, the base plate 1 has a flat outer face 4 on the outer side facing away from the core. On its outer edge the base plate has teeth 5 extending vertically outwards away from the outer face 4. The teeth 5 serve to engage or lock the prosthesis in an adjacent wall of a vertebral body. The inner side opposite the outer face 4 of the base plate has a concave recess 6. The concave recess 6 is preferably constructed as a spherical segment. Adjoining and encircling a concave recess 6 is an edge zone 7. The edge zone 7 is parallel to the outer face 4.

As can be seen from FIG. 2, the top plate 2 is constructed identically to the base plate 1. However, the top plate 2 is arranged as mirror-symmetrical to the base plate 1. Therefore, the concave recess 6' of the top plate 2 faces the concave recess 6 of the base plate 1.

Between base plate 1 and top plate 2 is the intervening core 3. This intervening core 3 has a central part 9 arranged symmetrical to the symmetry axis 8. The intervening core is in the form of a biconvex lens in which preferably, the convex outer faces have the same curve. Most preferably, the convex outer faces of the intervening core 3 have a spherical curve like the concave recesses 6, 6', so that the concave recesses 6 or 6' of the base plate and top plate, respectively can cooperate therewith.

As can further be seen from FIG. 2, the intervening core 3 also has an edge zone 10, the outer diameter of which is identical to the diameter of the base and top plates. The edge zone 10 is preferably constructed in such a way that the two faces facing the base plate and the top plate are constructed as parallel to one another and to the symmetrical plane of the intervening core.

As can further be seen from FIG. 2, the edge zone 10 of the intervening core 3 has an annular recess 11 on the underside facing the base plate 1 adjacent to the central part 9. In the embodiment shown this edge zone 10 has a cross-section shaped like a segment of a circle. The face opposite this of the edge zone 7 of the base plate has an annular recess 12 having the same diameter and in the embodiment shown likewise has a cross-section shaped like a segment of a circle.

As can be seen from FIG. 2, the surface of the edge zone 10 facing the top plate 2 is constructed as symmetrical to the side facing the base plate and has a corresponding annular recess 11'. The side of the top plate 2 facing the core, like the base plate 1, also has an annular recess 12' opposite annular recess 11', which corresponds in dimensions to annular recess 11'.

As seen from FIG. 2, rings 13 or 13' are arranged in the respective pairs 11, 12 or 11', 12' of the annular recesses.

The base plate 1 and the top plate 2 can be made of a biocompatible material. Preferably, the base plate 1 and the top plate 2 are made of steel or titanium, in particular of stainless steel 316L or a cobalt chrome alloy or titanium implant grade. According to a first embodiment the intervening core 3 is formed from a body-compatible high-molecular polyethylene synthetic material or any other suitable biocompatible polymer or other biocompatible material. Preferably the core is made of a high molecular weight polyethylene of the UHMWPE type with a molecular weight preferably between $2 \times 10^6$ to $10 \times 10^6$. The two rings, 13 and 13', are formed from a body-compatible elastic synthetic material, for example medical grade silicone.

Figure 11:
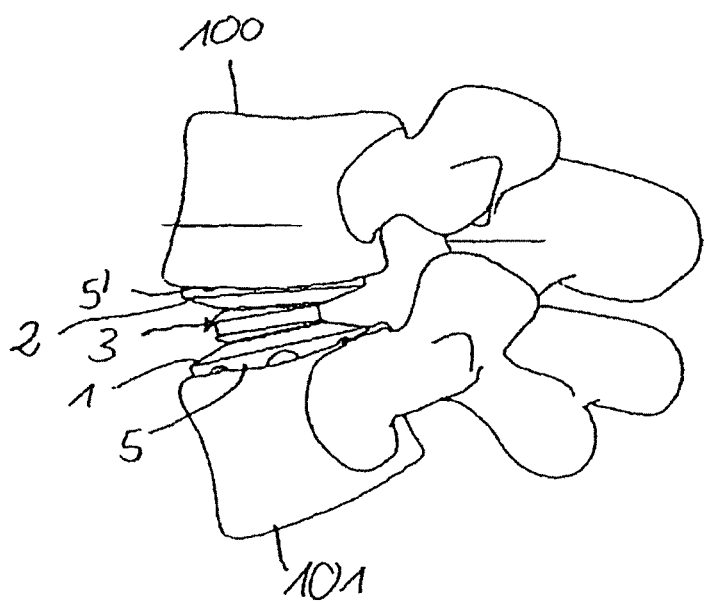
FIG. 11 shows a perspective view of the intervertebral disk prosthesis in the spinal column between two vertebrae.

The prosthesis of the present invention can be used in the following manner. First, the damaged intervertebral disk is surgically removed. Then the intervertebral disk prosthesis of the present invention is inserted between two vertebral bodies 100, 101 as shown in FIG. 11. The teeth 5, 5' of the prosthesis engage the walls of the adjacent vertebral body, so the bottom and top plates themselves are held fixed against rotation. The rings 13, 13' provide cushioning of the intervertebral disk prosthesis against over-severe tilting and simultaneously curb over-severe twisting about the central axis 8.

Preferably, the outer diameter of base and top plates is chosen in such a way that it is slightly smaller, preferably 10%-15% smaller, than the smallest diameter of the adjacent vertebral body end plate face.

Additional embodiments of the intervertebral disk prosthesis are shown in FIGS. 3, 4 and 5. In each of these embodiments, the prosthesis is also constructed as mirror-symmetrical about the central plane extending perpendicular to the symmetrical axis 8.

The second embodiment of the intervertebral disk prosthesis shown in FIGS. 3 and 4 also has a base plate 21, a top plate 22 and an intervening core 23 between the top plate and the base plate.

The base plate 21 has teeth 25 projecting vertically outwards from the base plate. The outer face 24, as can best be seen from FIG. 4, is constructed as a convex surface shaped like a segment of a sphere, wherein the curve of the surface is chosen in such a way that it substantially corresponds to a typical concave curve of a vertebral body end plate face to be brought into contact therewith. Symmetrical to the symmetrical axis 8 the surface facing the core has a concave recess 26 corresponding to concave recess 6. A first edge zone 27 is provided in the base plate. This first edge zone 27 is tapered off in the shape of a truncated cone towards the outer side of the base plate 21.

As can be seen from FIG. 4, the top plate 22 is constructed identically to the base plate and arranged as mirror-symmetrical to a central plane extending perpendicular to the symmetrical axis 8. The top plate includes teeth 25'.

The core 23 is constructed in three parts. The core comprises of two planar-convex lenticular bodies 28, having planar faces. The planar faces of the bodies 28 face each other. A coplanar plate 29 is arranged between the two planar faces. The lenticular bodies 28, 28' and the plate 29 have substantially the same diameter. The curve of the convex faces of the lenticular bodies corresponds to the curve of the concave recesses 26, 26' cooperating therewith.

As can best be seen from FIG. 4, the core 23 has a bore 30 extending perpendicular to its symmetrical plane and going through its central point. In this embodiment, the base plate and the top plate have continuous recesses 31, 31' extending along their symmetrical axes, providing for a continuous bore which extends from the base plate, through the core and to the top plate. In addition, both the top plate and the base plate on their outer faces 24, 24', have a countersunk bore, 32, 32', surrounding the recess 31, 31'. The countersunk bore extends the diameter of the recess on the outer face of the top plate and base plate respectively. A connecting sleeve 33 can be found in the bore 30. The connecting sleeve 33 is preferably made of a body-compatible synthetic material or of metal, for example stainless steel 316L or titanium implant grade. The diameter of the connecting sleeve is smaller than the diameter of the bore 30 and its length greater than the length of the bore 30, so the connecting sleeve engages with the respective open end in the recess of the adjacent top plate and bottom plate. As can be seen from FIG. 4, the sleeve 33 is constructed as tapered in each case towards its ends. A screw 34, 34' is screwed into the connecting sleeve 33 from both sides, guided in each case through the recesses 31, 31' wherein the head of the screw always rests in the countersunk bore of the top plate and bottom plate. The countersunk bore is slightly larger than the respective head of the screw. The screws are tightened to such an extent that base plate, top plate and core are connected to one another in such a way that the adjacent faces are held without play but are rotatably movable with respect to one another.

As can be seen from FIG. 4, the depth of the countersunk bores 32, 32' is slightly larger than the thickness of the heads of the screws 34, 34'. The countersunk bores are covered towards the outside at their outer end by cover plates 35, 35'. The difference between the depth of the countersunk bores 32, 32' and the thickness of the heads of the screws 34, 34' is chosen in such a way that the heads do not quite come up against the cover plates 35, 35' when the intervertebral disk prosthesis is elastically pressed.

The base plate and top plate are preferably constructed of the same material as described above with respect to the base plate and top plate of the first embodiment. The lenticular bodies 28, 28' preferably are made from the same material as the base and top plates. Plate 29 is formed from a body-compatible elastic synthetic material, preferably a medical grade silicone or medical grade silicone rubber. In this way the lenticular bodies together with the base and top plates take on the tilting motion that the intervertebral disk prosthesis is subject to while plate 29 takes care of the elasticity and therefore provides cushioning for the prosthesis.

The embodiment shown in FIG. 5 differs from the embodiment shown in FIGS. 3 and 4 only in the construction of the core. All other parts coincide with the previously described embodiment.

In this embodiment, the core 43 again has two outer plan-convex lenticular bodies 48, 48', which cooperate with the base and top plates with their convex faces in the same way as previously described. The central bore and the fastening by means of the connecting sleeve and the screws also is the same as with the previous embodiment. However, in this embodiment, an elastic ring 49 is provided as opposed to the plan-parallel plate 29. In order to accommodate and hold the elastic ring 49, the plan faces of the lenticular bodies 48, 48' facing one another have annular recesses 50, 50', shaped in cross-section as segments of a circle, in which the ring 49 is held.

The materials and the mode of operating and fitting correspond to the previously described embodiment. In this embodiment, the elastic ring 49 takes on the function of the plan-parallel plate 29.

In the embodiment shown in FIG. 6, the top plate is the same as the top plate described with in the embodiment of the intervertebral disk shown in FIG. 4. Although in FIG. 6 the outer face 54' is illustrated as flat, it can also be constructed as a convex corresponding to face 24', as shown in FIG. 4.

The base plate 51 is constructed differently in the embodiment of FIG. 6 as compared to the embodiment of FIG. 4. The base plate 51 is a cylindrical element which has on its side facing the top plate, a flat face 57 with a diameter which is identical to the diameter of the top plate. On its side facing away from the top plate, a cylindrical section 58 adjoins the flat face 57 with a diameter which is slightly smaller, preferably 5%-10% smaller, than the diameter of the flat face, so the section with larger diameter located above forms a stop. A cylindrical casing 59 surrounds section 58 as can best be seen in the perspective illustration in FIG. 7. The cylindrical casing 59 is snuggly placed around section 58. The cylindrical casing 59 has on its open end teeth 55 which can be brought into engagement with the adjacent vertebral body. The cylindrical casing 59 also has recesses 60 which substantially improve the ability to grow in. The shape and pattern of the recesses is, for example, described in U.S. Pat. Nos. 4,820,305 and 5,702,451 which are incorporated herein by reference.

The core 53 has on its side facing the top plate 52 a planar-convex lenticular body 61, corresponding to the lenticular body 28' of FIG. 4 in form and material. On the side facing away from this lenticular body a coplanar plate 62 is provided between its planar surface and the flat surface 57 of the base plate 51. The connection shown only schematically in FIG. 6 between base plate 51 and top plate 52 with the core 53 in between is constructed in the same way as in the two previously described embodiments. In this embodiment the movement takes place via the sliding pair of lenticular body 61 and top plate 52. Plate 62 provides for the damping.

In FIG. 8 a horizontal plan view of the top plate of the embodiments described in FIGS. 3 to 7 is shown. The cover plate 35' and the head of the screw 34' having been omitted from this view.

From FIG. 8, it can be seen that sleeve 33 may be hexagonal at its tapered ends. The faces between the six corners of the hexagon form channels. The respective recess 31' accommodating this hexagonal shape can also be constructed as a hexagon. The respective diameter of the recess 31' through two opposite corners is made slightly larger by a predetermined amount, preferably between 2% and 5% larger in each case than the corresponding diameter of the connecting sleeve at the same point. The faces between two corners in each case are constructed as bulging towards the center of the recess, the radius of the bulging curve being in each case slightly larger by a predetermined size, preferably by 2% to 5%, than the radius of the channels.

Figure 9:
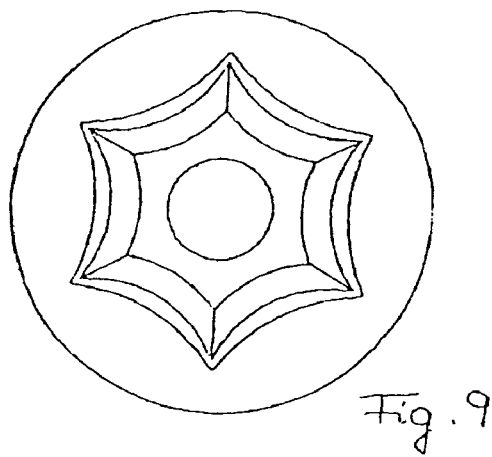
Figure 10:
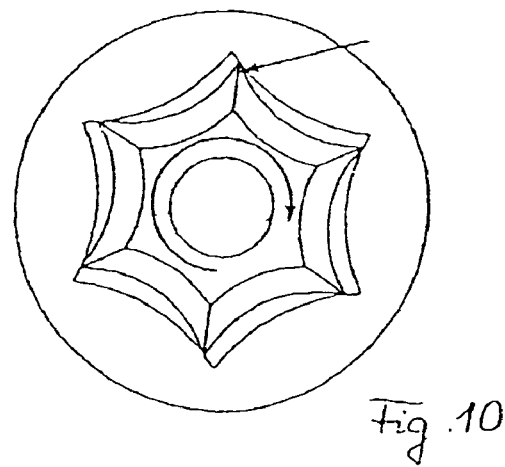

As shown in FIG. 9 and FIG. 10, a rotation by a measure predetermined by the differences in size can thus take place between sleeve and top plate or sleeve and base plate. The corners of the hexagonal section of the sleeve each form a mandrel abutting against the respective face of the recess 31'. In this way limitation of the rotation to a predetermined angle, preferably between 2° and 5°, is achieved.

In all the embodiments shown the outer faces of base and top plate can be formed as unpolished or rough textured surface in order to achieve improvement of cell ingrowth into the prosthesis.

In all the above-described embodiments, any of the adjacent faces carrying out a relative movement with respect of one another can be coated with appropriate material to facilitate or improve sliding between the parts. Examples of suitable coatings include ceramic layers, polyethylene coatings or appropriate metal alloys, preferably polished metal alloys.

Figure 12:
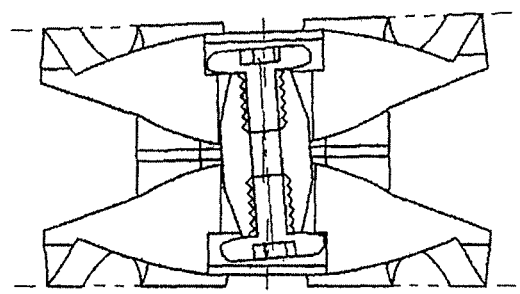
FIG. 12 shows a cross-sectional view of a further embodiment of the intervertebral disk prosthesis.

In the above-described embodiments, concave and convex spherical faces adjacent to one another and cooperating with each other are described. In each case the intervening core has the convex faces while the top plate and the base plate have associated concave spherical faces. According to a further embodiment of the present invention, the face shapes can be reversed in each case. In other words, the intervening core can be constructed as a biconcave lenticular body or as a plan-concave lenticular body and the associated contact face of base plate and top plate is then constructed as spherically convex corresponding to the concave spherical face. For example, FIG. 12 illustrates a further embodiment of the intervertebral disk prosthesis similar to the second embodiment shown in FIGS. 3 and 4, except the intervening core is constructed as a biconcave lenticular body, and the corresponding faces of the base plate and top plate are constructed as convex corresponding to the concave surfaces of the core.

Although the invention has been described and illustrated with reference to specific illustrative embodiments thereof, it is not intended that the invention be limited to those illustrative embodiments. Those skilled in the art will recognize that variations and modifications can be made without departing from the true scope and spirit of the invention as defined by the claims that follow. It is therefore intended to include within the invention all such variations and modifications that fall within the scope of the appended claims and equivalents thereof.

The invention claimed is:

1. An intervertebral disk prosthesis for use in the vertebral column, comprising:
    a base plate;
    a top plate;
    a core arranged in between the base plate and the top plate and being in contact with the base plate and the top plate, wherein the core has a curved surface on a side facing the top plate and a curved surface on a side facing the base plate, the curved surfaces forming sliding faces;
    the top plate having a curved section in sliding engagement with the curved surface of the core facing the top plate;
    the base plate having a curved section in sliding engagement with the curved surface of the core facing the base plate;
    wherein the core comprises an upper body defining the curved surface on the side facing the top plate, a lower body defining the curved surface on the side facing the base plate and an annular intermediate elastic body between and separating the upper and lower bodies to provide cushioning for the prosthesis;
    wherein the sliding engagements provide for respective rotational movement of the top plate and the base plate substantially about a central axis of the core extending from the upper body to the lower body, and respective sliding movement of the top plate and the base plate with respect to the core from first positions where respective axes of rotation of the top plate and the base plate form first angles with the central axis of the core to second positions where the respective axes of rotation of the top plate and the base plate form second angles with the central axis of the core;
    wherein the intermediate elastic body is configured to extend primarily in a plane generally perpendicular to the vertebral column; and
    wherein the prosthesis is configured to replace the vertebral disk.

2. The intervertebral disk prosthesis according to claim 1, the top plate having an outer edge and the base plate having an outer edge, wherein the base plate and the top plate each have teeth on their outer edges extending vertically outwards away from the core to engage in an adjacent wall of a vertebra in the vertebral column.

3. The intervertebral disk prosthesis according to claim 1, wherein along the central axis of the core a mandrel is provided to limit the relative movement between the base plate and the top plate about the central axis of the core.

4. The intervertebral disk prosthesis according to claim 1, wherein the base plate is cylindrical in shape to accommodate a cylindrical casing that is operable to be placed on the cylindrical base plate.

5. The intervertebral disk prosthesis according to claim 4, wherein the cylindrical casing has two opposite ends and teeth located in one of its ends to engage an adjacent wall of a vertebral body.

6. The intervertebral disk prosthesis according to claim 1, wherein the curved section of the top plate is concave.

7. The intervertebral disk prosthesis according to claim 1, wherein the curved section of the base plate is concave.

8. The intervertebral disk prosthesis according to claim 1, wherein the annular intermediate elastic body has a bore extending therethrough in a direction from the lower body to the upper body and the lower body and the upper body are located outside the bore.

9. The intervertebral disk prosthesis according to claim 1, wherein the respective first angles and the corresponding second angles have different sizes.

10. An intervertebral disk prosthesis for use in the vertebral column, comprising:
   a base plate;
   a top plate;
   a core arranged in between the base plate and the top plate and being in contact with the base plate and the top plate, wherein the core has a curved surface on a side facing the top plate and a curved surface on a side facing the base plate, the curved surfaces forming sliding faces;
   the top plate having a curved section in sliding engagement with the curved surface of the core facing the top plate;
   the base plate having a curved section in sliding engagement with the curved surface of the core facing the base plate;
   wherein the core comprises an upper body defining the curved surface on the side facing the top plate, a lower body defining the curved surface on the side facing the base plate and an intermediate elastic body between and separating the upper and lower bodies to provide cushioning for the prosthesis;
   wherein the intermediate elastic body is configured to extend primarily in a plane generally perpendicular to the vertebral column;
   wherein the prosthesis is configured to replace the vertebral disk; and
   wherein the core has a bore extending from the base plate through the intermediate elastic body to the top plate and wherein a connecting sleeve is provided within the bore of the intermediate elastic body to engage the base plate and the top plate.

11. The intervertebral disk prosthesis according to claim 10, wherein at least one screw is screwed into the connecting sleeve to connect the base plate, the top plate, and the core to each other.

12. The intervertebral disk prosthesis according to claim 10 wherein the sliding engagements provide for rotational movement of the top plate and the base plate substantially about a central axis of the core extending from the upper body to the lower body, and respective sliding movement of the top plate and the base plate from first angular positions relative to the central axis of the core to second angular positions relative to the central axis of the core.

13. The intervertebral disk prosthesis according to one of claim 1, 2, 3, 10 or 11 wherein the curved sections of the base plate and the top plate are constructed as convex and the curved surfaces of the core are constructed as concave.

14. The intervertebral disk prosthesis according to one of claim 1, 2, 3, 10 or 11 wherein the curved sections of the base plate and the top plate are constructed as concave and the curved surfaces of the core are constructed as convex.

15. An intervertebral disk prosthesis for use in the vertebral column, comprising:
   a base plate;
   a top plate;
   a core arranged in between the base plate and the top plate and being in contact with the base plate and the top plate, wherein the core has a curved surface on a side facing the top plate and a curved surface on a side facing the base plate, the curved surfaces forming sliding faces;
   the top plate having a curved section in sliding engagement with the curved surface of the core facing the top plate;
   the base plate having a curved section in sliding engagement with the curved surface of the core facing the base plate;
   wherein the core comprises an upper body defining the curved surface on the side facing the top plate, a lower body defining the curved surface on the side facing the base plate and an annular intermediate elastic body between and entirely separating the upper and lower bodies to provide cushioning for the prosthesis;
   wherein the sliding engagements provide for respective rotational movement of the top plate and the base plate substantially about a central axis of the core extending from the upper body to the lower body, and respective sliding movement of the top plate and the base plate with respect to the core from first positions where respective axes of rotation of the top plate and the base plate form first angles with the central axis of the core to second positions where the respective axes of rotation of the top plate and the base plate form second angles with the central axis of the core;
   wherein the intermediate elastic body is configured to extend primarily in a plane generally perpendicular to the vertebral column; and
   wherein the prosthesis is configured to replace the vertebral disk.

16. The intervertebral disk prosthesis according to claim 15, wherein the respective first angles and the corresponding second angles have different sizes.

* * * * *